(12) United States Patent
Kuth

(10) Patent No.: US 6,798,201 B2
(45) Date of Patent: Sep. 28, 2004

(54) MAGNETIC RESONANCE APPARATUS WITH SOUND INSULATION

(75) Inventor: Rainer Kuth, Herzogenaurach (DE)

(73) Assignee: Siemens Aktiengesellschaft, Münich (DE)

( * ) Notice: Subject to any disclaimer, the term of this patent is extended or adjusted under 35 U.S.C. 154(b) by 40 days.

(21) Appl. No.: 09/972,161

(22) Filed: Oct. 5, 2001

(65) Prior Publication Data

US 2002/0082496 A1 Jun. 27, 2002

(30) Foreign Application Priority Data

Oct. 5, 2000 (DE) .......................................... 100 49 414

(51) Int. Cl.[7] ................................................ G01V 3/00
(52) U.S. Cl. ...................................... 324/317; 324/318
(58) Field of Search ................................ 324/319, 318, 324/309, 307

(56) References Cited

U.S. PATENT DOCUMENTS

| 4,652,824 A | * | 3/1987 | Oppelt ........................ 324/318 |
| 5,489,848 A | * | 2/1996 | Furukawa ................... 324/318 |
| 5,793,210 A | | 8/1998 | Pla et al. .................... 324/318 |
| 6,043,653 A | | 3/2000 | Takamori et al. ........... 324/318 |
| 6,414,489 B1 | * | 7/2002 | Dean et al. ................. 324/318 |

FOREIGN PATENT DOCUMENTS

| DE | 38 33 591 | | 10/1988 |
| DE | 198 38 390 | | 8/1998 |
| DE | 19838390 | * | 3/2000 |
| EP | 0 138 269 | | 4/1985 |
| EP | 1 077 382 | | 2/2001 |

\* cited by examiner

Primary Examiner—Brij B. Shrivastav
(74) Attorney, Agent, or Firm—Schiff Hardin LLP

(57) ABSTRACT

A magnetic resonance apparatus disposed in an installation space has a first component group, which contain at least a basic field magnet system and a gradient coil system, a second component group, which contains an examination volume for receiving an object under investigation and which has at least one supporting device for bringing the object under investigation supported thereon into the examination volume, and sound insulation arranged between the first and second component groups so that the installation space is divided into two spaces which are sound-insulated from each other, a first of the spaces containing the first component group and a second of the spaces containing the second component group.

12 Claims, 1 Drawing Sheet

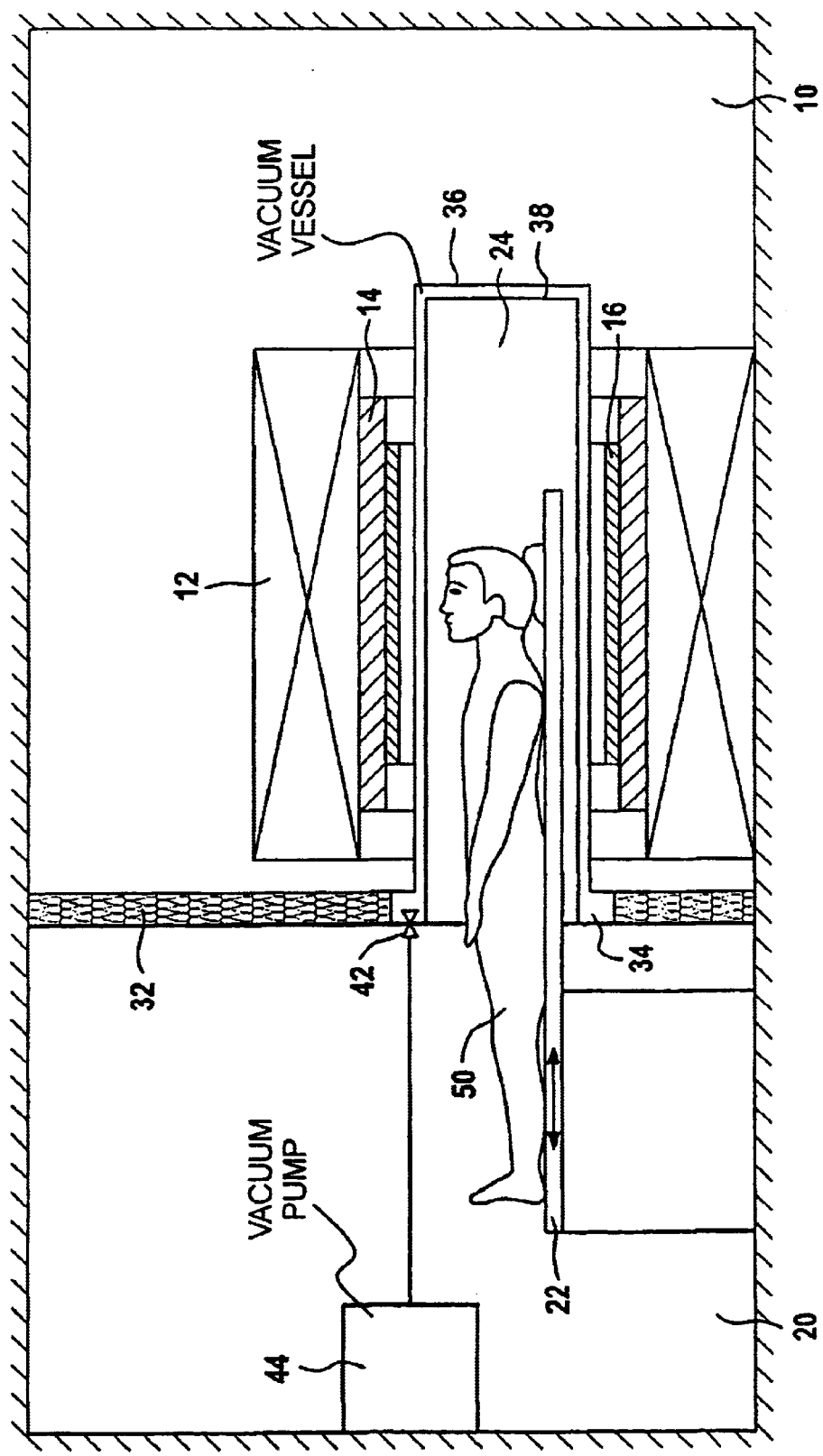

MAGNETIC RESONANCE APPARATUS WITH SOUND INSULATION

BACKGROUND OF THE INVENTION

1. Field of the Invention

The present invention relates to a magnetic resonance apparatus, and in particular to a magnetic resonance apparatus with an arrangement for insulating sound from the examination subject.

2. Description of the Prior Art

Magnetic resonance is a known technique for obtaining images of the inside of the body of an object under investigation. For this purpose, a magnetic resonance apparatus has a space for receiving the object under investigation, known as an investigation space. A basic field magnet system of the apparatus generates a static magnetic field that is as homogeneous as possible, at least in a region of the investigation space. Rapidly switched gradient fields, which are generated by a gradient coil system of the apparatus, are superimposed on the basic magnetic field. In this case, currents of amplitudes which reach several 100 A flow in the gradient coils, and the frequent and rapid changes in the direction of the current are subject to rates of rise and fall of several 100 kA/s. These currents are controlled on the basis of pulse sequences and, in the presence of a base magnetic field of the order of 1 T, cause oscillations or vibrations of the gradient coil system due to Lorentz forces.

These oscillations are passed on to the entire surface of the magnetic resonance apparatus over various propagation paths. Depending on the surface speed, the vibrations of the mechanical system of the various surface regions are transformed into acoustic vibrations, which ultimately cause noise that is disturbing.

A further development in the field of magnetic resonance technology for reducing the measuring times and improving imaging properties involves faster sequences. These bring about an increase in the current amplitudes and the rates of current rise and fall in the gradient coils. Without countermeasures, this leads to larger Lorentz forces and more rapid changing of the direction in which the Lorentz forces act, then to stronger vibrations and in turn to more noise. In this way, the noise reaches peak values of, for example, up to 130 dB and is consequently above the tolerance limit of patients.

In German OS 38 33 591 a magnetic resonance apparatus is disclosed wherein the hollow-cylindrical gradient coil system of which is arranged inside a cavity of a basic field magnet system without mechanical connections with the basic field magnet system. The gradient coil system is adjustably supported by a supporting framework, which is arranged outside the basic field magnetic system, so that mechanical decoupling of the two systems is achieved. This arrangement, however, does not prevent noise originating from the vibrations of the gradient coil system from being emitted into an examination volume space of the apparatus.

In U.S. Pat. No. 4,652,824 discloses a magnetic resonance apparatus with a superconducting base field magnet system which has a vacuum enclosure. In this case, a gradient coil system of the apparatus for reducing noise development is arranged in a specially isolated manner in the vacuum enclosure. Nevertheless, vibrations of the gradient coil system can be transmitted via fastenings of the gradient coil system to the basic field magnet system to a surface of the apparatus, where they are transformed into noise.

In European Application 0 138 269 discloses a magnetic resonance apparatus with a hollow-cylindrical basic field magnet system, in the cavity of which a hollow-cylindrical gradient coil system is arranged, in the cavity of which in turn a sleeve is concentrically arranged, forming a noise-absorbing shield between the gradient coil system and an examination volume of the apparatus. In one embodiment, an intermediate space between the sleeve and the gradient coil system is designed for this purpose in such a way that it can be evacuated. Nevertheless, vibrations of the gradient coil system can be transmitted via fastenings of the gradient core system to the basic field magnet system to a surface of the apparatus, where they are transformed into noise.

In U.S. Pat. No. 5,489,848 discloses a magnetic resonance apparatus with a hollow-cylindrical base field magnet system, in the cavity of which a substantially cylindrical device is arranged and designed in such a way that it forms a substantially hollow-cylindrical vacuum vessel toward the basic field magnetic system. A gradient coil system of the apparatus is arranged in the vacuum vessel. Nevertheless, vibrations of the gradient coil system can be transmitted via fastenings of the gradient coil system to the basic field magnet system to a surface of the apparatus, where they are transformed into noise.

In German OS 197 34 138 discloses a magnetic resonance apparatus having a gradient coil system arranged in a vacuum enclosure to reduce noise. In this case, the gradient coil system within the vacuum enclosure is supported by a number of vibration-damping fastenings arranged at intervals. Nevertheless, vibrations of the gradient coil system can be transmitted via the fastenings of the gradient coil system to the vacuum enclosure, which in turn is fastened on the basic field magnetic system, to a surface of the apparatus, where they are transformed into noise.

U.S. Pat. No. 6,043,653 discloses a magnetic resonance apparatus in which a gradient coil system and a basic field magnetic system are set up independently of each other on a base, and as a result are substantially decoupled from each other, and the gradient coil system is additionally arranged in a vacuum enclosure.

SUMMARY OF THE INVENTION

An object of the present invention is to provide an improved magnetic resonance apparatus in which noise affecting an object under investigation can be reduced in a highly effective and low-cost way.

The object is achieved in accordance with the invention in a magnetic resonance apparatus disposed in an installation space, the apparatus having a first component group, which includes at least a basic field magnet system and a gradient coil system, a second component group, which includes (defines) examination volume for receiving an object under investigation and which includes at least one supporting device for bringing the object under investigation supported thereon it into the examination volume, and a sound insulation, which is arranged between the first and second component groups to divide the installation space into two spaces which are sound-insulated from each other, a first of the spaces containing the first component group and a second of the spaces containing the second component group.

As a result, it is possible by a comparatively minor modification of commercially available magnetic resonance apparatuses to achieve a noise reduction of more than 40 dB for the object under investigation in a low-cost way.

DESCRIPTION OF THE DRAWING

The single FIG. 1 is a side view, partly in section, of a magnetic resonance imaging apparatus constructed and operating in accordance with the principles of the present invention.

DESCRIPTION OF THE PREFERRED EMBODIMENTS

The FIG. 1 shows, as an exemplary embodiment of the invention, a longitudinal section of a magnetic resonance apparatus arrangement. The magnetic resonance apparatus has a first component group, which includes a basic field magnet system 12 for generating a base magnetic field, a gradient coil system 14 for generating gradient fields and an antenna system 16 for radiating radio-frequency signals into a patient 50 and for receiving magnetic resonance signals thereby triggered. In this case, the basic field magnet system 12, the gradient coil system 14 and the antenna system 16 are of a substantially hollow-cylindrical form. The gradient coil system 14 is in this case arranged concentrically in a cavity of the basic field magnet system 12, and the antenna system 16 is in turn arranged concentrically in a cavity of the gradient coil system 14. A vacuum vessel 34 extends into a remaining cavity of the first component group.

The vacuum vessel 34 is designed as a cylindrical double-wall vessel, which has an outer vessel wall 36 and an inner vessel wall 38. Between the two vessel walls 36 and 38, therefore arranged concentrically in relation to each other, is a vacuum. The vacuum vessel 34 is provided with a valve 42, via which the vacuum vessel 34 can be evacuated by a vacuum pump 44 connected to the valve 42. This is required, for example, to evacuate a vacuum vessel 34 that is not seamless to its rated vacuum quality, for example after a certain amount of time has passed or following installation work. In another embodiment, in which the vacuum vessel 34 is of a seamless configuration, for example as a result of hermetic welding, it is possible to dispense with the valve 42 and the vacuum pump 44.

The open side of the vacuum vessel 34 is joined to a substantially circular opening of a heavy sound-insulating wall 32. Together with the sound-insulating wall 32, the vacuum vessel 34 represents an interface between a first space 10, which contains the first component group, and a second space 20, which contains an examination volume 24 for receiving the patient 50. In this case, the two spaces 10 and 20 are separated from each other in a sound-insulating manner by the vacuum vessel 34 together with the sound-insulating wall 32.

In order to prevent direct mechanical transmission of vibrations can take place from the first component group to the vacuum vessel 34 and the sound-insulating wall 32, the vacuum vessel 34 and the sound-insulating wall 32 have no direct contact surfaces with the first component group. Consequently, vibration transmission is only possible via intermediate layers of air and via a base of the space 10. The vibrations transmitted to the base of the space 10 are damped due to the heaviness of the base so that vibration propagation is substantially prevented. The same applies to vibrations coupled in via the air of the space 10 to the sound-insulating heavy wall 32 and the remaining ceilings and walls of the space 10. Vibrations coupled in via the air to the outer vessel wall 36 of the vacuum vessel 34 are not transmitted to the inner vessel wall 38, facing the second space 20, because of the vacuum. It is important in this case that the outer vessel wall 36 and the inner vessel wall 38 are configured and fastened in such a way that they are vibration-decoupled from each other at the opening of the sound-insulating wall 32, so that no vibration transmission between the vessel walls 36 and 38 takes place at this point either. Furthermore, the vessel walls 36 and 38 are made from a material which does not disruptively influence the magnetic resonance imaging and/or appears transparent in the magnetic resonance images, for example a glass-fiber and/or aramid-fiber reinforced plastic.

A cavity of the vacuum vessel 34 substantially forms the examination volume 24, in which a region to be imaged of the patient 50 to be investigated is appropriately positioned for a magnetic resonance investigation. For this purpose, a movable supporting device 22 of the magnetic resonance apparatus, on which the patient 50 can be supported, is arranged in the second space 20. By moving the supporting device 22 appropriately, the aforementioned positioning can be carried out. The supporting device 22 is in this case configured in such a way that it withstands torsional moments caused by patients.

Although modifications and changes may be suggested by those skilled in the art, it is the intention of the inventor to embody within the patent warranted hereon all changes and modifications as reasonably and properly come within the scope of his contribution to the art.

I claim as my invention:

1. An installation for a magnetic resonance apparatus comprising:
    a first component group including a basic field magnet system and a gradient coil system;
    a second component group, including an examination volume adapted to receive an examination subject, and a support device adapted to move said examination subject into and out of said examination volume;
    an installation space in which said first component group and said second component group are installed; and
    sound insulation disposed between said first component group and said second component group to divide the installation space into two portions of said space which are acoustically insulated from each other, said first component group being installed in a first of said portions and said second component group being installed in said second of said portions.

2. An installation for a magnetic resonance apparatus as claimed in claim 1 wherein said first component group has no direct contact surfaces with said sound insulation.

3. An installation for a magnetic resonance apparatus as claimed in claim 1 wherein said sound insulation comprises a vacuum vessel.

4. An installation for a magnetic resonance apparatus as claimed in claim 3 wherein at least a portion of said vacuum vessel is disposed adjacent to said examination volume.

5. An installation for a magnetic resonance apparatus as claimed in claim 1 wherein said sound insulation includes an insulation portion adjacent to said examination volume consisting of a material which does not disruptively influence magnetic resonance imaging.

6. An installation for a magnetic resonance apparatus as claimed in claim 5 wherein said material is selected from the group consisting of glass fiber reinforced plastic and aramid-fiber reinforced plastic.

7. An installation for a magnetic resonance apparatus as claimed in claim 1 wherein said sound insulation comprises a heavy sound-insulating wall.

8. An installation for a magnetic resonance apparatus as claimed in claim 7 wherein said heavy sound-insulating wall is a wall of said installation space.

9. An installation for a magnetic resonance apparatus as claimed in claim 7 wherein said heavy sound-insulating wall has an opening adapted to allow passage of said examination subject therethrough.

10. An installation for a magnetic resonance apparatus as claimed in claim 9 wherein said sound insulation includes a vacuum vessel substantially enclosing said examination volume and joined to said opening.

11. An installation for a magnetic resonance apparatus as claimed in claim 1 wherein said sound insulation completely physically separates said two portions of said installation space from each other.

12. A method for installing a magnetic resonance apparatus comprising the steps of:

employing a sound insulation to divide an installation space into two portions of said installation space which are acoustically insulated from each other;

installing a first component group, including a basic field magnet system and a gradient coil system, of a magnetic resonance apparatus in a first of said two portions of said installation space; and installing a second component group, including an examination volume adapted to receive an examination subject, and a support device adapted to move said examination subject into and out of said examination volume, of said magnetic resonance apparatus in a second of said two portions of said installation space.

* * * * *